(12) United States Patent
Fang et al.

(10) Patent No.: US 7,691,580 B2
(45) Date of Patent: Apr. 6, 2010

(54) REVERSE PROTEIN DELIVERY INTO CELLS ON CODED MICROPARTICLES

(75) Inventors: Ye Fang, Painted Post, NY (US); Brian L. Webb, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 1472 days.

(21) Appl. No.: 10/353,496

(22) Filed: Jan. 29, 2003

(65) Prior Publication Data
US 2004/0146944 A1   Jul. 29, 2004

(51) Int. Cl.
*G01N 33/53* (2006.01)
(52) U.S. Cl. ........................................ 435/7.1; 436/518
(58) Field of Classification Search .................. 435/7.1, 435/7.2, 92
See application file for complete search history.

(56) References Cited

U.S. PATENT DOCUMENTS

| | | | |
|---|---|---|---|
| 5,008,116 A * | 4/1991 | Cahn ........................... | 424/491 |
| 5,512,474 A * | 4/1996 | Clapper et al. ............... | 435/402 |
| 5,547,841 A | 8/1996 | Marotta et al. | |
| 5,601,980 A | 2/1997 | Gordon et al. | |
| 5,731,152 A | 3/1998 | Maracas et al. | |
| 5,807,522 A | 9/1998 | Brown et al. | |
| 6,544,790 B1 | 4/2003 | Sabatini | |
| 6,632,928 B1 * | 10/2003 | Neville et al. .......... | 530/388.75 |
| 7,105,347 B2 | 9/2006 | Fang et al. | |
| 2002/0137059 A1 * | 9/2002 | Wu et al. ........................ | 435/6 |
| 2003/0119207 A1 * | 6/2003 | Dejneka et al. .............. | 436/524 |
| 2003/0124029 A1 | 7/2003 | Webb et al. | |
| 2006/0105371 A1 | 5/2006 | Fang et al. | |

FOREIGN PATENT DOCUMENTS

| | | | |
|---|---|---|---|
| WO | WO 00/16893 | * | 3/2000 |
| WO | WO 00/62815 | | 10/2000 |
| WO | WO 00/63419 | | 10/2000 |
| WO | WO 01/20015 | | 3/2001 |
| WO | 02/14860 | | 2/2002 |
| WO | WO 02/37944 | | 5/2002 |
| WO | 03/076588 | | 9/2003 |

OTHER PUBLICATIONS

Kasuya et al. J Biomaterials Science 1993 vol. 4, p. 369-380.*
Scorilas et al. (Clin. Chem. 2000 vol. 46, p. 1450-1455).*
Vaisanen et al. (Luminescence 2000 vol. 15, p. 389-397).*
Harma et al. (Clinical Chem 2000 vol. 46, p. 1755-1761).*
Dr. Simon Goldbard, "Simultaneous Interrogation of Multiple Receptors by Non-Positional Cell Arrays", Virtual Arrays, Inc., presentation at the Cell-Based Microarrays & High Content Screening, Mar. 20, 2002, San Diego, CA.

(Continued)

*Primary Examiner*—Jacob Cheu
(74) *Attorney, Agent, or Firm*—John L. Haack; Thomas R. Beall

(57) ABSTRACT

Systems, methods and kits that utilize uniquely coded microparticles for performing protein assays are provided. The uniquely coded microparticles are used as a substrate for reverse protein delivery into cells. The microparticles and methods offer the possibility of studying the biological functions of either a single protein of interest in multiple cell types per assay or multiple proteins in a single cell type.

27 Claims, 2 Drawing Sheets

OTHER PUBLICATIONS

Steven R. Schwarze et al., "Protein transduction: unrestricted delivery into all cells?", Trends in Cell Biology, vol. 10, Jul. 2000, p. 290-295.

A. Lalvani et al., "Rapid Effector Function in CD8+ Memory T Cells", J. Exp. Med., vol. 186, No. 6, Sep. 15, 1997.

Daniel D. Clark et al., "Rapid Detection of Protein Tyrosine Kinase Activity in Recombinant Yeast Expressing a Universal Substrate", Journal of Proteome Research, 2002, vol. 1(3).

Joanne D. Andreadis et al., "Use of Immobilized PCR Primers to Generate Covalently Immobilized DNAs for In Vitro Transcription/Translation Reactions", Nucleic Acids Research, 2000, vol. 28, No. 2, pp. i-viii.

Mingyue He et al., Single Step Generation of Protein Arrays from DNA by Cell-Free Expression and in Situ Immobilisation (PISA method), Nucleic Acids Research, 2001, vol. 29, No. 15, pp. 1-6.

Junaid Ziauddin et al., "Microarrays of Cells Expressing Defined cDNAs", Nature, vol. 411, May 3, 2001, pp. 107-110.

Stephen L. Hussey et al., "Efficient Delivery of Streptavidin to Mammalian Cells: Clathrin-Mediated Endocytosis Regulated by a Synthetic Ligand", Journal of Am. Chem. Soc. 2002, vol. 124, pp. 6265-6273.

Olivier Zelphati et al., "Intracellular Delivery of Proteins with a New Lipid-Mediated Delivery System", The Journal of Biological Chemistry, vol. 276, No. 37, Sep. 14, 2001, pp. 35103-35110.

G. MacBeath et al., "Printing Proteins as Microarrays for High-Throughput Function Determination", Science, vol. 289, Sep. 8, 2000, pp. 1760-1763.

D. Derossi et al., "Trojan Peptides: the Penetratin System for Intracellular Delivery", Cell Biology, vol. 8, Feb. 1998, pp. 84-87.

Alberts et al., Molecular Biology of the Cell, 3rd Edition, Eds, Garland Publishing, 1994, p. 22.

Fox, Richard M., et al., "Incorporation of Deoxynucleotides into DNA by Diethylaminoethyldextran-Treated Lymphocytes", Biochemistry, vol. 16, No. 20, 1977.

Rigby, Perry G., "Prolongation of Survival of Tumour-bearing Animals by Transfer of "Immune" RNA with DEAE Dextran", Nature, vol. 221, p. 968-969, Mar. 9, 1969.

Amersham 2001 catalog on DEAE-Dextram (2001) pp. 1-4.

* cited by examiner

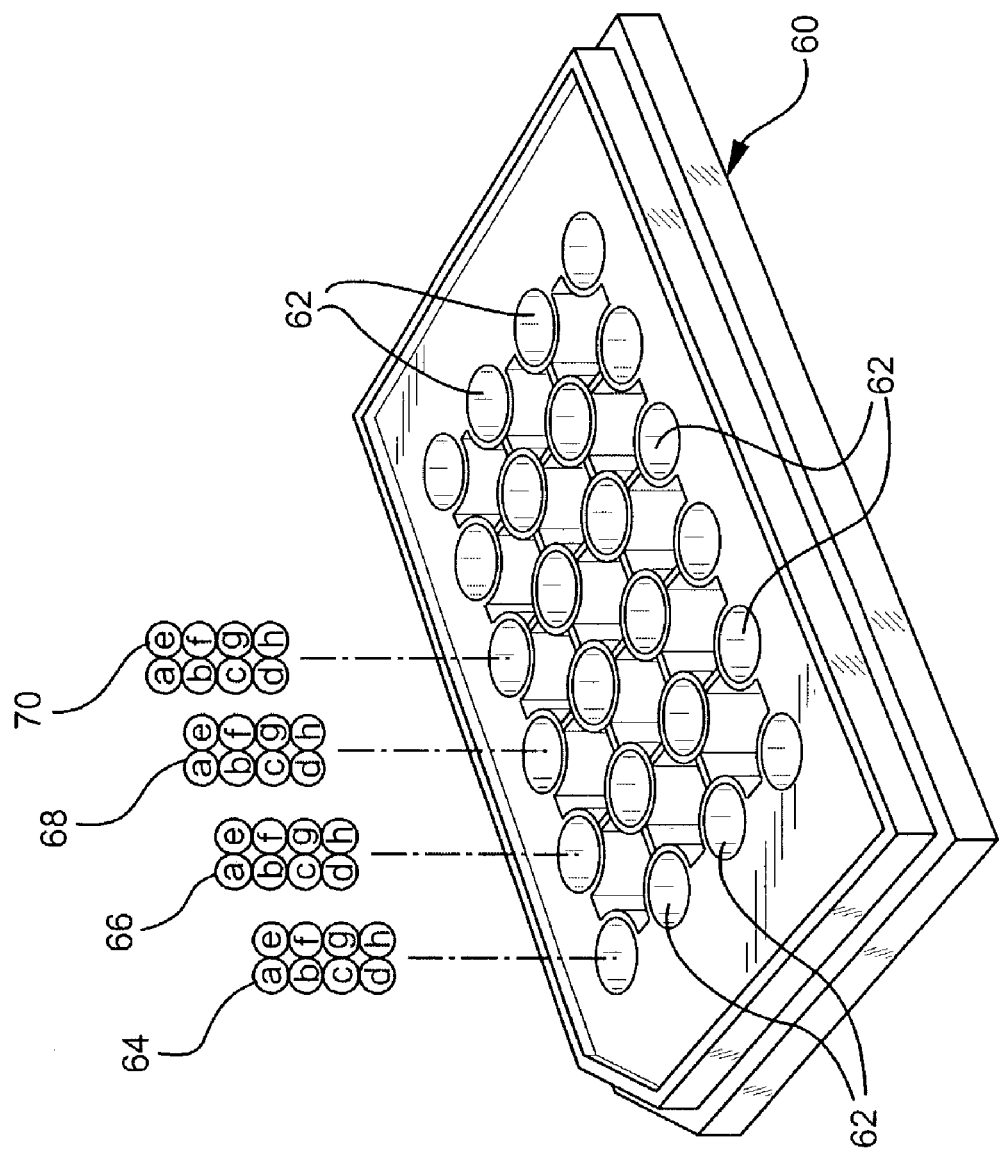

REVERSE PROTEIN DELIVERY INTO CELLS ON CODED MICROPARTICLES

FIELD OF THE INVENTION

The present invention relates to biological assays. More particularly, the invention pertains to methods and articles for reverse protein delivery into living cells using coded microparticles.

BACKGROUND OF THE INVENTION

Systematic- and proteomic-wide studies of the biological functions of proteins have drawn increasing interest during the past several years as the realization that mRNA expression levels may not accurately reflect the activity/expression level of their corresponding protein. And proteins, not genes, are the true targets of modern medicines. The prevailing approach for analyzing protein function in vivo is use of cell-based assays. These types of assays are used to study the function of one particular gene in a cellular context by gene transfection and protein delivery.

Protein delivery, which is known in the art as protein transduction, is the process by which a peptide or protein motif is delivered across the plasma membrane into the cell. Traditionally, methods to introduce antibodies, peptides or other membrane-impermeable molecules into cells include microinjection and electroporation. The obvious disadvantages of these techniques are that they tend to be toxic to the recipient cells, they are non-specific (i.e., anything can enter or exit the cell once the membrane is disrupted), and they exhibit low transduction efficiency and substantial variability. To overcome the disadvantage associated with these techniques, researchers have developed a number of protein-transduction domains (PTDs) that mediate protein delivery into cells. These PTDs or signal peptide sequences are naturally occurring polypeptides of 15 to 30 amino acids, which normally mediate protein secretion in cells. They are composed of a positively charged amino terminus, a central hydrophobic core and a carboxyl-terminal cleavage site recognized by a signal peptidase. Recently, researchers have shown that a number of membrane-translocating peptides can successfully mediate delivery of polypeptides, protein domains, and full-length protein, including antibodies into cells using solution-based protein transduction protocols. Recently, researchers have also demonstrated the use of lipid liposomes or the like for protein delivery. Traditionally, however, these approaches have been limited since they are solution-based formats. Only one gene or protein may be studied per assay. As there are more than 35,000 genes present in the human genome, and approximately 10,000 of these genes are expressed as proteins in any given cell type, a high-throughput method for studying gene function is needed. It would be desirable to provide systems, including, but not limited to, methods, microparticles, and kits for multiplexed analysis protein and cell interaction within a single experiment.

SUMMARY OF THE INVENTION

The invention relates to systems, methods and kits that utilize uniquely coded microparticles for delivering protein into cells. According to certain embodiments of the invention, uniquely coded microparticles are used as a substrate for reverse protein delivery into cells. The microparticles and methods offer the possibility of studying the biological functions of either a single protein of interest in multiple cell types per assay or multiple proteins in a single cell type.

Advantages of the invention will be apparent from the following detailed description. It is to be understood that both the foregoing general description and the following detailed description are exemplary and are intended to provide further explanation of the invention as claimed.

BRIEF DESCRIPTION OF THE DRAWINGS

FIG. 2 is a schematic view of a microplate and a plurality of coded microparticles for multiplexed screening according to one embodiment of the invention.

DETAILED DESCRIPTION

Figure 1:
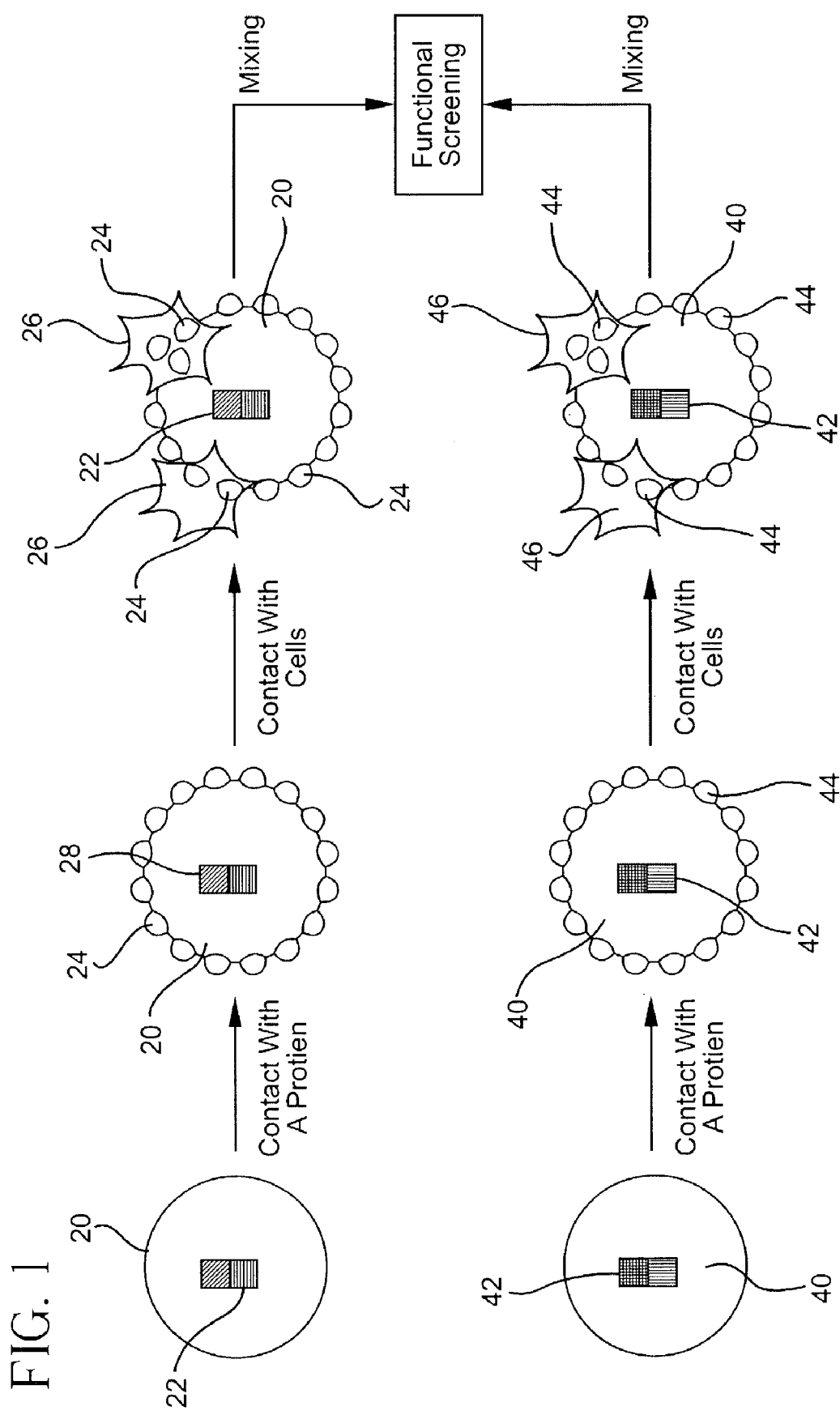
FIG. 1 is a schematic view of microparticles contacted with a protein that can be delivered into cells according to one embodiment of the invention.

Before describing several exemplary embodiments of the invention, it is to be understood that the invention is not limited to the details of construction or process steps set forth in the following description. The invention is capable of other embodiments and of being practiced or carried out in various ways.

The invention relates to systems, methods and kits including uniquely coded particles for cell analysis. Certain embodiments of the invention provide uniquely coded microparticles used as a substrate for reverse protein delivery into cells. Other embodiments relate to methods that use uniquely coded microparticles in which proteins are reverse delivered to cells. Delivery of proteins to cells can occur by contacting microparticles with a protein-containing mixture that includes a protein of interest, and then contacting the microparticles with cells under conditions sufficient to deliver the proteins to the cells. The microparticles can be used in high-throughput analysis of protein functions in prokaryotic or eukaryotic cells (e.g., bacterial, mammalian, human, insect, or plant cells). The microparticles may be used for rapid and direct functional screening of protein or enzymatic functions or any given intracellular protein interaction in the natural environment of a living cell. Moreover, the microparticles also are useful for high-throughput screening of other biological and chemical analytes, such as drugs, which affect the functions of these proteins.

According some embodiments of the invention, proteins can be pre-complexed with membrane-disrupting pore-forming reagents and placed in contact with microparticles, or can be pre-complexed with specific receptor-binding reagents and placed in contact with microparticles. Cells are then placed in contact with the microparticles including the proteins bound thereto, which then uptake the proteins. Unlike reverse transfection methods that are limited to genes that encode proteins, the reverse protein delivery can be used to deliver a broad range of protein-like biomolecules, including functional peptides, protein domains, proteins, protein mutants, engineered proteins with specific modifications, antibodies, and particle-protein conjugates.

As used herein, the term "contact" or "contacted" means attaching a protein or a cell to a microparticle directly or indirectly by a linking group through a binding mechanism. Binding mechanisms for proteins include, but are not limited to ionic bonding, hydrogen bonding, electrostatic interaction, van der Waals interactions, and/or hydrophilic-hydrophobic interaction. Binding mechanisms for cells include, but are not limited to, biospecific binding, for example, cells adhere onto a surface through the interaction between RGD peptides presented on a surface and cell surface receptors.

As used herein, "code," "coded," and "encoded" refers to association of identifying information with a microparticle to identify the microparticle. The identifying information could be information about cells and/or biomolecules in contact with the microparticles. For example, if microparticles are individually in contact with a single, different protein, the code could contain information to identify each protein in contact with each microparticle. The code could be based on the size, shape, or other physical property of the microparticle such as density, weight, color, plurality of colors, fluorescence, or other detectable property. In certain preferred embodiments, the code is based on a detectable optical property associated with the microparticles. In other preferred embodiments, the microparticles are encoded with at least one rare earth element. In embodiments in which rare earth elements are used to encode the particles, the coding could be based on the quantity, size, or type of rare earth element associated with a particle. The particles could be encoded with two or more rare earth elements to provide a barcode. The rare earth elements can be separated spatially to provide a pattern or array similar to a bar code. Each of the different rare earth elements, or same elements doped at a different concentration or location on the particle provides a discrete optical signal upon illumination capable of detection by conventional optical equipment and can be used to identify the particle. Rare earth elements are preferred because certain rare earth elements, do not spectrally interfere with traditional fluorescent channels such as Cy3, Cy5, Texas Red, FITC, and other fluorescent reporter dyes. For example, a particle coded with $Eu_2O_3$ produces red fluorescence, a particle coded with $Tb_2O_3$ fluoresces green, and a particle code with $Tm_2O_3$ or $CeO_2$ fluoresces blue. These rare earth elements are exemplary only, and a wide variety of other rare earth elements could be used in accordance with the present invention. In addition, mixtures of rare earth could be used to produce a wider variety of fluorescent colors. The particles containing rare earth elements can be excited with a mercury lamp at either 254 or 365 nm. At these wavelengths, fluorescent tags such as the commonly used Cy-3 and Cy-5 are not excited, and therefore, crosstalk and interference between these common fluorescent tags and the particles encoded with rare earth elements does not occur.

As used herein, the term microparticle means a small piece of material that can be used as a host or a carrier for conducting reverse protein delivery experiments on a surface of the microparticle. The microparticle can be in shape of sphere, cylinder, circular disk, square plate, or any irregular-shaped disk. Commercially available microparticles range in size tens of microns to thousands of microns in diameter. Examples of suitable microparticles include glass, metal, ceramic, or polymeric beads. The uniquely coded microparticle, according to one specific embodiment, is a small piece of glass uniquely coded with rare earth metals or other state-of-the-art microbarcode methods. The uniquely coded microparticle, in another embodiment, is a macroporous and/or microporous microparticle with a code embedded inside the particle, such as cytodex™, cytoline™, cytopilot™ mini™, cytopore™, and the like, which are available from Amersham. These commercially available cyto carriers do not have a code embedded inside, however, these carriers can be further modified with state-of-the-art methods to embed a code inside them. Cytodex™ microcarriers are based on cross-linked dextran beads. The microporous beads are transparent, spherical and hydrated, and are substituted with positively charged groups. Cytodex™ microcarriers have a mean diameter of 200 μm and a density of 1.04 g/ml. Their small size allows them to be easily transported through tubing. Cytoline™ microcarriers are based on a matrix of polyethylene and silica. The polyethylene makes the microcarrier hydrophobic whilst the silica gives it a slightly negatively charge. Cytoline microcarriers are lentil-shaped with a length of 2 to 2.5 mm. This size makes their transfer through tubing more difficult, but possible. Cytopore™ microcarriers are hydrophilic and have a mean diameter of 230 μm and a density of 1.03 g/ml. They are based on a cross-linked cotton cellulose matrix and have an average pore size of 30 μm. Cytopore™ microcarriers are both macroporous and microporous. Cytopore™ microcarriers are easily transported through tubing.

The unique coding information on the microparticles can be embedded inside the microparticle using a variety of state-of-the-art methods. For example, a nanobarcoded glass bead can be encapsulated inside the host microparticle. In another embodiment, a DNA or protein delivered into the cells can serve as the barcode. A non-uniquely coded microparticle coated with a protein of interest is directly used to deliver protein to cells, and the resulting cells themselves can be indirectly or directly used as a barcode due to the expressed protein. For example, different proteins can be labeled with different fluorescent dyes, quantum dots, gold nanoparticles, paramagnetic nanoparticles, silica nanoparticles or other nanoparticles. In another embodiment, a uniquely coded molecule is mixed with the protein to be delivered into cells and used as a code. For example, purified green fluorescent protein or yellow fluorescent protein can be mixed with a protein of interest and co-delivered onto a microparticle host. Alternatively, different cell types can be co-transducted with DNAs encoded with different fluorescent proteins, such as green fluorescent protein (GFP) or yellow fluorescent protein (YFP). In another alternative, the protein delivered into the cell could be fused to a protein that serves as an identifier. Examples of such fusion proteins include a GFP fusion protein. The fluorescence of these proteins can be used as a barcode.

FIG. 1 is a schematic view according to one embodiment of the present invention. FIG. 1 shows a first microparticle 20 and a second microparticle 40. The first microparticle includes a unique identification code 22, and second microparticle includes a unique identification code 42. As shown in FIG. 1, the unique identification codes 22, 42 include a colored barcode pattern comprising at least two different colors. The embodiment shown in FIG. 1 illustrates one of many ways that particles can be marked with a unique identification code. According to certain embodiments, the unique identification code is used to identify a characteristic or the identity of a protein associated with the microparticles 20, 40. For example, if two different proteins of interest were being assayed, code 22 would identify a first protein associated with microparticle 20, and code 42 would identify a second protein associated with the microparticle 40. In certain embodiments, the proteins may be functionally related. In other embodiments, the proteins may the same type of protein but have different point mutations. In another embodiment, the microparticles 20, 40 could be associated with the same protein, and the microparticles 20, 40 bound to the proteins could be used to study interaction with two different cell types. According to this embodiment, the codes 22, 42 would represent first and second cell types.

Still referring to FIG. 1, the microparticles 20, 40 are placed in contact with protein-containing mixtures such that a protein 24 is bound to the first microparticle 20, and a protein 44 is bound to the second microparticle 40. In the embodiment shown in FIG. 1, different proteins are bound to the first and second microparticles. After the proteins have been bound to the microparticles 20 and 40, cells 26, 46 are then placed in contact with the microparticles 20 and 40 in a manner such that protein is delivered to the cells. For example, mammalian cells are cultured on the mixture-coated surface. The cells take-up the protein(s), which may affect cellular functions or observable events.

According to certain embodiments, the microparticles of the present invention can be used to provide a system or kit for multiplexed screening of proteins that could include reagents, microparticles and other equipment to perform multiplexed screening, for example, a microplate. Referring to FIG. 2, a multiwell plate 60 have a plurality of wells 62 can be used for contacting a plurality of groups of different microparticles 64a-h, 66a-h, 68a-h, 70a-h, etc., each microparticle attached to a different protein of interest. After each microparticle has been placed in its respective well, cells can be cultured in each of the multiwell plates under conditions such that the proteins in each well are delivered to the cells. Thereafter, the microparticles can be removed from the wells for functional screening. In certain embodiments, the same type of cell is cultured in each well of the multiwell plate. In other embodiments, the microparticles in each well are contacted with the same protein of interest, and different cell types are cultured in each of the different wells.

Proteins can be delivered to cells according to a "reverse delivery" technique in which a mixture containing: 1) a protein-of-interest, or 2) a protein-of-interest complexed with a carrier reagent, or 3) a protein-of-interest-conjugate with a carrier reagent, or 4) a combination thereof, is contacted with the microparticle and so that the proteins are bound to the surface of the microparticle. Cells are placed in contact with the microparticles including proteins, wherein the microparticle bearing the protein is used to culture the cells. Under appropriate conditions, the proteins enter the cells.

Proteins may include intracellular proteins, cell surface proteins, toxin proteins, antibodies, synthetic peptides, bioactive peptides, and protein domains; also protein-nucleic acid conjugates, and protein-nanoparticle conjugates, or multi-protein complexes. Additionally, conjugates between a protein-organic chemical entity or protein-inorganic chemical entity (e.g., Biotin, fluorescent dyes, silage derivatives, mass spectrometry tags, or low-molecular weight chemical moiety, etc.) are included.

Examples of intracellular proteins include, but are not limited to: oxidoreductases, transferases, hydrolases, lyases, isomerases, ligases, kinases, phosphoproteines, and mutator transposons, DNA or RNA associated proteins (for example, homeobox, HMG, PAX, histones, DNA repair, p53, RecA, robosomal proteins, etc.), electron transport proteins (for example, flavodoxins); adaptor proteins; initiator caspases, effector caspases, inflammatory caspases, cyclins, cyclin-dependent kinases, cytoskeletal proteins, G-protein regulators, small G proteins, mitochondria-associated proteins, PDZ adaptor proteins, PI-4-kinases, etc. Recombinant proteins of unknown functions may also be used.

Applicable cell surface proteins include, but are not limited to: G-protein coupled receptors (e.g. the aderenergic receptor, angiotensin receptor, cholecystokinin receptor, muscarinic acetylcholine receptor, neurotensin receptor, galanin receptor, dopamine receptor, opioid receptor, erotonin receptor, somatostatin receptor, etc), G proteins, ion-channels (nicotinic acetylcholine receptor, sodium and potassium channels, etc), receptor tyrosine kinases (e.g. epidermal growth factor (EGF) receptor), immune receptors, integrins, and other membrane-bound proteins. Mutants or modifications of such proteins or protein functional domains or any recombinant forms of such proteins may also be used.

Toxin proteins include, but are not limited to, cholera toxin, tetanus toxin, shiga toxin, heat-labile toxin, botulinum toxin A & E, delta toxin, pertussis toxin, etc. Toxin domains or subunits may also be used. Antibodies include, but are not limited to, organism-specific antibodies such as mouse and human antibodies, monoclonal and polyclonal antibodies, intact antibodies or single-chain antibodies.

Synthetic and bioactive peptides and protein domains also can be delivered to cells using the method of the present invention. Amino acid sequences described herein are referred to by a sequence identifier number (SEQ ID NO:). The SEQ ID NOs correspond numerically to the sequence identifiers <400>1, <400>2, etc. The Sequence Listing in written format and on the computer readable form (CRF), which is a single compact disc, are incorporated by reference in their entireties. For example, a synthetic peptide comprising a sequence of AAYANAAVE (SEQ ID NO: 3) may be delivered to cells and monitor the protein tyrosine kinase (PTK) activity in cells. This peptide has recently been used as a universal PTK substrate for rapid detection of PTK activity in recombinant yeast (Clark, D. D. & Peterson, B. R., J. Am. Chem. Soc., 1, 207-209 (2002)). Foreign proteins such as streptavidin and lectins and polymers may also be used.

Nanoparticle-protein conjugates may be delivered to proteins and used to deliver proteins to and visualize cells. The particles can include fluorescent tags, quantum dots, gold nanoparticles, paramagnetic nanoparticles, silica nanoparticles, or beads of silica glass or polymer material, or the like. In other embodiments, protein-DNA conjugates are used. The DNA can be directly used as a code or be used to encode a unique protein.

In another embodiment, proteins immobilized on the surface of the microparticle are preferably originated (produced) by using in vitro translation of nucleic acids previously deposited on the surface. In another embodiment, the proteins are preferably synthesized on the surface in situ. After the protein is synthesized on a surface of a microparticle, it can then be mixed with a carrier material to allow the protein to be delivered into cells after the cells become contact with the surface.

A library of fusion proteins can be deposited on a plurality of microparticles, and then adherent cell lines can be placed in contact with the microparticles. By this method, it is possible to assess the function of the protein in vivo in eukaryotic cells. Interactions between the delivered protein and other native cellular proteins may be studied in vivo. Fusing the delivered protein with an auto-fluorescent marker, such as the green fluorescence protein (GFP), may monitor intercellular localization of the delivered protein. Reverse delivery into cells could be accomplished, for instance, using VP22 fusion protein, herpes simplex protein, or any other protein with the similar properties. The fusion protein can be made using state-of-the-art methods. Some commercially available vectors for the production of VP22 fusion protein in mammalian cells and *Escherichia coli* (for example, pVP22/myc-His-2 from Invitrogen, Carlsbad, Calif.) are applicable. The fusion protein can be deposited directly and affixed onto microparticle, or the fusion protein can be pre-mixed with a helper reagent and then deposited and affixed onto the microparticle for delivery to cells.

According to certain embodiments of the invention, particular vehicle or carrier reagents are used to facilitate reverse protein delivery or reverse transduction. Carrier reagents may comprise a variety of reagents. In one embodiment, the carrier reagent is a bioactive cell membrane-permeable reagent, or other peptides containing protein-transduction domains (PTDs) (i.e., single peptide sequences comprising about 15 to about 30 residues). Protein-transduction domains (PTDs) mediate protein secretion, and are composed of a positively charged amino terminus, a central hydrophobic core and a carboxyl-terminal cleavage site recognized by a single peptidase. Examples of such membrane-transducing peptides include Trojan peptides, human immuodeficiency virus (HIV)-1 transcriptional activator (TAT) protein or its functional domain peptides and other peptides containing protein-transduction domains (PTDs) derived from translocation proteins such as Drosophilia homeotic transcription factor Antennapedia (Antp) and herpes simplex virus DNA-binding protein, VP22, and the like. Some commerically available peptides, for example, penetratin 1, Pep-1 (Chariot reagent, Active Motif Inc., Calif.) and HIV GP41 fragment (519-541), can be used.

Other carrier reagents include signal sequences, which have been used efficiently to target proteins to specific locations in both prokaryotic and eukaryotic cells, and a number of membrane-translocating peptides. Membrane-translocating peptides have been applied successfully to mediate membrane-translocation and the importation of a polypeptide, protein domain, full-length protein, or antibody into a cell using standard solution-based delivery protocols. The carrier reagent is a bioactive peptide or ligand that can specifically bind to and activate cell surface receptors. After binding to the cell surface receptors, the receptor and bound carrier-protein complex will undergo internalization, resulting in the delivery of ligand-protein complexes into cells. The proteins may be complexed with the ligand beforehand or in situ. The ligand can be complexed with the protein of interest or the protein to be introduced into cells by means of non-covalent interaction such as hydrophobic interaction or electrostatic interaction or both, or coupled covalently to the protein, or by means of a ligand-receptor binding interaction. For example, a carrier reagent can be modified with a ligand that can bind specifically to the protein of interest. To illustrate, a synthetic ligand termed "Streptaphage" has efficiently delivered streptavidin to mammalian cells by promoting non-covalent interactions with cholesterol and sphingolipid-rich lipid raft subdomains of cell plasma membranes (Hussey, S. L. & Peterson, B. R., J. Am. Chem. Soc., 124, 6265-6273 (2002)).

In another embodiment, the carrier reagent is a lipid liposome or any other reagent that can complex with a protein of interest and promote the delivery of the protein into the cell. The carrier reagent could be a naturally occurring or synthetic lipid. For example, the protein encapsulated in the formulation binds to the negatively vehicle lipids for delivery (O. Zelphati et al., J. Bio. Chem., 276, 35103-19 (2001)). Products available commercially can be used, such as BioPORTER (Gene Therapy Systems), or ProVectin (Imgenex, San Diego, Calif.).

Protein delivery reagents (e.g., Chariot™ by Active Motif, or BioPORTER® by Gene Therapy Systems) can help save time by bypassing the traditional DNA transfection, transcription and protein translation processes associated with gene expression. Depending on the nature of the particular reagent employed, fusion proteins or chemical coupling in some embodiments would not be needed. The reagent forms a complex with the protein, stabilizes the macromolecule and protects it from degradation during delivery. Once internalized in a cell, the complex can dissociate, leaving the macromolecule biologically active and free to carry out its biological function.

Certain embodiments involve the use of at least one helper reagent. In one embodiment, the helper reagent is a polymer such as DEAE-dextran, dextran, polylysine, and polyethylamine. In another embodiment, a helper reagent can also be a cell adherent-enhancing protein, such as fibronectin and gelatin. The helper reagent can be a sugar-based compound (e.g., polyethylene glycol) or a synthetic or chemical-based gelatin, such as acrylamide. In a further embodiment, the helper reagent can be a RGD peptide, such as Arg-Gly-Asp-Ser (SEQ ID NO: 1), Arg-Gly-Asp-Ser-Pro-Ala-Ser-Lys-Pro (SEQ ID NO: 2), and the like. Alternatively, the helper reagent can be a mixture of a hydrogel and a RGD peptide, and combination of any the aforementioned molecules. The use of helper reagents enhances the efficiency of protein delivery into the cells.

In one embodiment involving a reverse protein delivery method, the protein-containing mixture comprises protein and a vehicle reagent that is present in an appropriate solvent, such as phosphate silane buffer. The mixture is incubated with a microparticle for certain time under appropriate conditions, and washed to remove excess mixture in solution. This results in a microcparticle bearing (having affixed or bound thereto) a protein-containing mixture.

In one embodiment, uniquely coded microparticles having a set of different proteins of interest bound to the microparticles are independently used to transduct or deliver protein to a single cell type. After delivery of the proteins to the cells, the microparticles carrying the cells containing the proteins are mixed together for rapid and direct screening the functions of the multiple proteins or any given intracellular proteins interacting with these proteins, as well as for high-throughput screening of drugs on these proteins in a given single cell type. In another embodiment, uniquely coded microparticles are preferably contacted with a single protein of interest, and used to deliver protein to multiple cell types independently. After delivery of the protein to the cells, the microparticles carrying the protein-bearing cells are mixed together for rapid and direct screening the functions of the single protein or any given intracellular proteins interacting with this protein, as well as for high-throughput screening of drugs on this protein in multiple cell types.

Reverse protein delivery on uniquely coded microparticles allows for screening of multiple protein targets within a single experiment. For example, by placing a mixture of 25 unique uniquely coded microparticles with 25 different proteins within the wells of a 96-well microplate and carrying out surface-mediated delivery, these 25 different targets can be screened simultaneously within each well in a high throughput fashion for drug interactions, ligand binding, etc. Another advantage of using uniquely coded microparticles is that the same protein can be studied in multiple cell types. This is accomplished by separately contacting multiple cell types on uniquely coded microparticles coated with the same protein followed by mixing the microparticles together in a common well.

The use of uniquely coded microparticles as a platform for carrying out reverse protein delivery affords flexibility compared to the conventional array format. Using uniquely coded microparticles allows the assembly of arrays within the well of a microplate by adding any desired combination of coated microparticle-protein elements. This allows flexibility in the content of the arrays to be manufactured, depending on the need and desire of the end-user/customer.

In addition, this flexibility also means a greatly simplified manufacturing process. Instead of having to contact print the protein in a predefined array pattern onto a solid support (e.g., a slide or microplate well), the protein can be applied to uniquely coded microparticles in bulk lots and then mixed together in the appropriate variety and ratios to form an array in the bottoms of a microplate wells.

Without intending to limit the invention in any manner, certain embodiments of the present invention will be more fully described by the following example.

EXAMPLE

Reverse Protein Delivery on Cytodex Microcarrier

In this example, three G protein-coupled receptors are used as model proteins to be delivered into cells using reverse protein delivery approach on coded microparticles. They are neurotensin receptor subtype I (NTR1), opioid receptor subtype mu and delta2. Rare earth metal doped glass beads obtained from the Coming Incorporated are used as the coded microparticles on which cells attach, grow, and uptake the pre-coated proteins to be delivered. The resulting protein-transducted cells are used for screening compounds that can effect cell signaling pathways.

Materials and Methods

Purified or unpurified recombinant human NTR1, mu and delta2 receptors are individually solubilized in 1% dodecyl maltoside using state-of-the-art methods (for example, discussed in Sklar, L. A. Vilven, J. Lynam, E. Neldon, D. Bennett, T. A., Prossnitz, E. "Solubilization and Display of G Protein-Coupled Receptors on Beads for Real-Time Fluorescence and Flow Cytometric Analysis" BioTechniques 2000, 28,976-985). Each solubilized receptor is pre-complexed with BioPORTER (Gene Therapy Systems). In some cases, helper reagent such as DEXE-dextran or RGD peptides is added into the mixture to enhance protein-delivery efficacy. The mixture is added to a well of 96-well microplate that contains 100 rare earth doped glass beads. These beads have a dimension of 20 micron in height, 50 micron in width and 200 micron in length, and have a unique code. After a 2 hour incubation and then wash, the beads are coated with the receptor-containing complexes. Three types of beads coated with different receptor-containing complexes are added into a same well in 24-well microplate. 250000 cells in serum-free medium are added into the cells. After 2 hours, serum media is used to replace serum-free media. Within a relative short of time (generally 1-3 hours) these cells become attached, and uptake the proteins pre-coated on these coded beads. The protein-transducted cells are ready for further studies. For example, these protein-transducted cells can be used for screening compounds that can selectively activate one of these three receptors in living cells by using state-of-the-art methods, such as Ca2+ flux fluorescence assays, fluorescence cAMP assays or beta-arrestin-GFP translocation assays.

The present invention provides several advantageous and unique aspects, which differentiate it from other processes, including the reverse transfection method. A surface-mediated protein delivery to living cells is able to transduct multiple proteins in a single assay using the array format over traditional, solution-based cell protein delivery techniques. This virtue provides for simultaneous, parallel analysis of many different proteins for a desired cellular readout (e.g., apoptosis, changes in cell morphology, effects on signaling pathway, etc.). Such a high-throughput capability signifies that many more proteins can be screened per assay. The ability to screen more proteins per assay also reduces the amount of reagents consumed per assay, which can greatly reduce assay costs.

Delivery of proteins into cells has certain advantages over delivering DNA into cells by transfection. Since the protein molecule itself is being delivering into the cell and not the precursor gene, the present technique bypasses the transcription-translation process associated with gene expression. Hence, the protein will begin performing its biological functions immediately after entry into the cell, greatly shortening the duration of time until cells can be assayed for protein function. The shorter time period (<24 hrs.) required to manifest the effects of the delivered protein in the cell is due in part to an ability to bypass the transcription and translation process associated with gene expression. This feature is another advantage of the present method. Typically, one can see changes within 12 hours. In some cases, greater than 95% of proteins can be delivered in as little as 3-6 hours, or even as short as within 1 or 2 hours.

Another advantage of the method is that it can be used to assess the role of post-translational modification (PTM) on protein functions. Previously in DNA transfection methods, a protein would be modified after translation according to specific signals on the protein (e.g., glycosylation sites), which would be dependent on the availability of a correct set of enzymes in the target cell line. The present method circumvents this need to find a cell line that will perform these PTMs. Using an array of the present device, one can test the effect that different PTMs in a protein (e.g., various sugar groups), which have been engineered in vitro, have on the biological function of the protein in a cell, without need to mutate the DNA sequence, or alter the signals and/or transfect the DNA into an appropriate cell line.

Moreover, unlike gene transfection that is limited to only the expression of gene products, the present protein delivery approach can be used to transfect cells with a much broader range of biologicals, for instance, including bioactive peptides, proteins domains, proteins, antibodies, protein-nucleic acid conjugates, antibody-nucleic acid conjugates, nanoparticle-protein conjugates, multi-protein complexes, and any amino-acid containing moiety.

Furthermore, the method can make amenable studies of the same protein in different cells (e.g., a protein in differentiated and undifferentiated stem cells). For instance, even though certain mammalian cells are notoriously difficult to transfect, of the mammalian cell types tested to date according to the present invention, all were receptive to protein transduction (delivery). Another advantage of the present method is the ability to better control the biological effect by varying the dosage or quantity of protein per cell.

It will be apparent to those skilled in the art that various modifications and variations can be made to the present invention without departing from the spirit or scope of the invention. Thus, it is intended that the present invention covers modifications and variations of this invention provided they come within the scope of the appended claims and their equivalents.

What is claimed is:

1. A method for delivering proteins in cells, comprising:
contacting a first micro-carrier substrate having a unique identification code with a first protein-containing mixture under conditions to allow the protein to attach to the micro-carrier substrate, wherein the first protein-containing mixture comprises a protein of interest, a carrier reagent, and a helper reagent; and
contacting the first micro-carrier substrate having the protein of interest attached thereto with cells under conditions sufficient for the cells to adhere to the surface of the micro-carrier substrate and for the cells to uptake the protein of interest, wherein the code on the first micro-carrier substrate includes at least one rare earth element.

2. The method of claim 1, wherein the micro-carrier substrate is contacted with the protein-containing mixture in a well.

3. The method of claim 1, further comprising contacting at least a second micro-carrier substrate having a unique identification code with a second protein-containing mixture under conditions sufficient to allow the second protein to attach to the second micro-carrier substrate and contacting the at least second micro-carrier substrate including a second protein bound thereto with cells under conditions sufficient to deliver the second protein into the cells in contact with the second micro-carrier substrate, the second protein-containing mixture comprises the second protein of interest, a carrier reagent, and a helper reagent.

4. The method of claim 3, wherein the second micro-carrier substrate is contacted with the second protein-containing mixture in a well.

5. The method of claim 1, wherein the at least one rare earth element is patterned on the first micro-carrier substrate.

6. The method of claim 5, wherein the first micro-carrier substrate is porous.

7. The method of claim 3, further wherein protein-containing mixture on the first micro-carrier substrate contains a first protein and the protein-containing mixture on the second micro-carrier substrate contains a second protein different from the first protein.

8. The method of claim 7, wherein the different proteins are functionally related.

9. The method of claim 3, wherein said proteins on the first and second micro-carrier substrates comprise the same protein of interest but with different point mutations.

10. The method of claim 7, wherein the first and second micro-carrier substrates are contacted with the same cell type.

11. The method of claim 10, wherein the first and second micro-carrier substrates are placed in different wells of a multiwell plate.

12. The method of claim 10, wherein the first and second micro-carrier substrates are screened for drug interactions or ligand binding.

13. The method of claim 1, comprising contacting a plurality of first micro-carrier substrates having the same protein bound thereto with a plurality of different cell types.

14. The method of claim 10, wherein said protein of interest includes a functional peptide, protein mutants, engineered proteins with specific modifications, antibodies, bioactive peptide, protein-domain, intracellular protein, enzyme, cell surface protein, toxin protein, antibody, antibody-nucleic acid conjugate, protein-nucleic acid conjugate, peptide-nucleic acid conjugate, protein-nanoparticle conjugate, protein-polymer conjugate, conjugate between a protein-organic chemical entity or protein-inorganic chemical entity, multi-protein complexes, and any amino-acid containing moiety.

15. The method of claim 10, wherein said protein of interest includes a fusion protein that contains a translocation domain and a protein domain of interest.

16. The method of claim 1, wherein the carrier reagent is a naturally occurring or synthetic translocation peptide, or a liposome.

17. The method of claim 1, wherein said carrier reagent includes: a bioactive cell membrane-permeable reagent, a membrane-translocating peptide, a peptide containing protein-transduction domains (PTDs), a signal sequence, a bioactive peptide, or a ligand that can bind specifically to and activate cell surface receptors.

18. The method of claim 1, wherein said carrier reagent includes: Trojan peptides, human immuodeficiency virus (HIV-1) transcriptional activator (TAT) protein or its functional domain peptides, Drosophilia antennapedia homeotic transcription factor, and herpes simplex virus-1 DNA binding protein VP22.

19. The method of claim 1, wherein said helper reagent includes: a polymer, a cell adherent-enhancing protein, a sugar-based gelatin, a synthetic or chemical-based gelatin, a RGD peptide, a mixture of a hydrogel and a Arg-Gly-Asp (RGD) peptide, or a combination of any the aforementioned molecules.

20. The method of claim 1, wherein said helper reagent is a polymer selected from the group consisting of: DEAE-dextran, dextran, polylysine, and polyethylamine.

21. The method of claim 1, wherein said helper reagent is a cell adherent-enhancing protein selected from the group comprising a fibronectin and gelatin.

22. The method of claim 1, wherein said helper reagent is either polyethylene glycol or acrylamide.

23. The method of claim 1, wherein said helper reagent is a RGD peptide selected from the group comprising of: (SEQ ID NO: 1), (SEQ ID NO: 2), and combinations thereof.

24. The method of claim 1, wherein the conditions for delivery include placing the first micro-carrier substrates in a serum-free medium.

25. The method of claim 1, wherein the conditions sufficient for delivery include placing a plurality of first micro-carrier substrates in a serum-containing medium.

26. The method of claim 1, wherein the first micro-carrier substrate is encoded with a co-delivered protein separately attached to the first micro-carrier substrate.

27. The method of claim 1, wherein the first micro-carrier substrate is encoded with a fusion protein associated with the protein of interest that uniquely identifies the protein attached to the first micro-carrier substrate.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: Artificial
<220> FEATURE:

-continued

```
<223> OTHER INFORMATION: Synthetic primer

<400> SEQUENCE: 1

Arg Gly Asp Ser
1

<210> SEQ ID NO 2
<211> LENGTH: 10
<212> TYPE: PRT
<213> ORGANISM: Artificial
<220> FEATURE:
<223> OTHER INFORMATION: Synthetic primer

<400> SEQUENCE: 2

Arg Gly Asp Ser Pro Ala Ser Ser Lys Pro
1               5                   10

<210> SEQ ID NO 3
<211> LENGTH: 9
<212> TYPE: PRT
<213> ORGANISM: Artificial
<220> FEATURE:
<223> OTHER INFORMATION: Synthetic primer

<400> SEQUENCE: 3

Ala Ala Tyr Ala Asn Ala Ala Val Glu
1               5
```